US005629305A

United States Patent [19]
Eek et al.

[11] Patent Number: 5,629,305
[45] Date of Patent: *May 13, 1997

[54] SYNERGISTIC COMBINATION OF A SUBSTANCE WITH GASTRIC ACID SECRETION INHIBITING EFFECT AND AN ACID DEGRADABLE ANTIBIOTIC

[75] Inventors: Arne T. Eek, Trosa; Sven Erik Sjöstrand, Södertälje, both of Sweden

[73] Assignee: ASTRA Aktiebolag, Sodertalje, Sweden

[*] Notice: The term of this patent shall not extend beyond the expiration date of Pat. No. 5,599,794.

[21] Appl. No.: 441,766

[22] Filed: May 16, 1995

Related U.S. Application Data

[62] Division of Ser. No. 51,722, Apr. 22, 1993.

[30] Foreign Application Priority Data

Apr. 24, 1992 [SE] Sweden ............................. 9201297
Jan. 8, 1993 [SE] Sweden ............................. 9300029

[51] Int. Cl.$^6$ ..................... A61K 31/43; A61K 31/44; A61K 31/335
[52] U.S. Cl. ..................... 514/199; 514/338; 514/450
[58] Field of Search ..................... 514/395, 450, 514/338, 199

[56] References Cited

U.S. PATENT DOCUMENTS 5,013,743  5/1991  Iwahi et al. .
5,407,688  4/1995  Place .

FOREIGN PATENT DOCUMENTS

WO9009175  2/1990  WIPO .
WO9204898  4/1991  WIPO .

OTHER PUBLICATIONS

Czinn et al, *Chemical Abstracts*, vol. 105, No. 17, abstract #149590m, 1986.
Tzelepi et al, *Biological Abstracts*, vol. 93, No. 2, abstract #14092, 1992.
Londong et al, *Biological Abstracts*, vol. 92, No. 5, abstract #56565, 1991.
Inatomi et al, *Chem. Abstracts*, vol. 115, No. 3, abstract #22001w, 1991.
Graham et al, *Biosis Abstract*, BR41: 125113, 1991.
McDermott, et al., *Science*, The Absorption of Orally Administered Penicillin, Mar. 22, 1946, pp. 359–361.
McNulty, et al., *Eur. J. Clin. Microbiol. Infect. Dis.*, Susceptibility of Clinical Isolates, Aug., 1988, pp. 566–569.
*The Lancet*, Clarithromycin and Omeprazole, vol. 340, Jul. 25, 1992, p. 239.
Goodwin, Worsley, Peptic Ulcer Disease, 1992, *Current Science*, 8:122–127.
Loo, Sherman, Matlow; Helicobacter pylori Infection, *Anti-microbial Agents & Chemotherapy*, May, 1992, pp. 1133–1135.
P. Unge, et al. "Does Omeprazole, 40 mg o.m. improve antimicrobial therapy directed towards gastric *Campylobacter–pylori* in patients . . . " Scandinavian Journal of Gastroenterology 1989, 24 (Suppl. 166) p. 184 (Abstract).
P. Unge, et al. "Does Omeprazole improve antimicrobial therapy directed towards gastric *Campylobacter–pylori* in patients with antral gastritis" Scandinavian Journal of Gastroenterology 1989, 24 (Suppl. 167) pp. 49–54 (Article).
"Which regimen for *H pylori* eradication?" SCRIP No. 1861, p. 23; Oct. 5, 1993.
S. Rune, "*Helicobacter pylori*, Peptic Ulcer Disease and Inhibition of Gastric Acid Secretion" Digestion 1992; 51 (Suppl. 1): 11–16.

*Primary Examiner*—Marianne M. Cintins
*Assistant Examiner*—William R. A. Jarvis
*Attorney, Agent, or Firm*—Nixon & Vanderhye

[57] ABSTRACT

A synergistic pharmaceutical combination and composition are disclosed for the treatment of gastritis and peptic ulcer containing a therapeutic amount of a proton pump inhibitor such as e.g., omeprazole or lansoprazole, which increases intragastric pH, and a therapeutic amount of an acid degradable antibacterial compound such as a penicillin or a macrolide. In particular, the combination is directed to the treatment of infections caused by *Helicobacter pylori* by raising the bioavailability of acid degradable antibacterial compounds.

19 Claims, 2 Drawing Sheets

SYNERGISTIC COMBINATION OF A SUBSTANCE WITH GASTRIC ACID SECRETION INHIBITING EFFECT AND AN ACID DEGRADABLE ANTIBIOTIC

This application is a divisional of application Ser. No. 08/051,722, pending filed on Apr. 22, 1993.

FIELD OF THE INVENTION

The present invention relates to a combination of a substance with inhibiting effect on the gastric acid secretion, thus a substance which increases the intragastric pH e.g. proton pump inhibitors, histamin-$H_2$-blockers and one or more antibacterial compounds which are acid degradable.

BACKGROUND OF THE INVENTION

In the treatment of the peptic ulcer disease current therapy aims at reducing the gastric acid secretion, thus resulting in a recess of the injuries in the gastro-intestinal tract. Inhibitors of the gastric acid secretion, proton pump inhibitors in particular, induce a rapid relief of pain and other symptoms associated with the ulcer disease. However, relapses of the disease is a documented fact. Since gastric antisecretory therapy only leads to reduction of the major tissue irritating factor, gastric acid, the plausible cause of the disease, *Helicobacter pylori*, remains mainly unaffected. (*Helicobacter pylori* was earlier named *Campylobacter pylori*.)

*Helicobacter pylori* is affected by certain antibiotic compounds e.g. macrolides and penicillins as has been shown in vitro and in vivo. However, these products are degraded into nonantibacterial metabolites in the presence of gastric acid, which drastically reduces their antibacterial efficacy.

In view of the widespread use of antimicrobial pharmaceuticals in the treatment of infectious diseases or for other purposes and the consequent emergence of drug-resistant strains, increased incidence of microbial substitution due to disturbance of the normal bacterial flora, changes in profile of infectious diseases, etc., there has been a constant demand for the development of new antimicrobial agents or combinations thereof.

PRIOR ART

Proton inhibitors e.g. omeprazole and its pharmaceutically acceptable salts, which are used in accordance with the invention, are known compounds, e.g. from EP 5129 and EP 124495 and can be produced by known processes. From U.S. Pat. No. 5,093,342 it is also known that omeprazole can be used in the treatment of Helicobacter infections. Further it has earlier been proposed in WO 92/04898 to use a specific antibiotic, amoxycillin, which is stable in gastric acid, in combination with pantoprazole in the treatment of duodenal ulcers. No specific test data are included in said document.

From e.g. Science, Mar. 22, 1946, p. 359–361 it is known that if acid degradable penicillins are administered orally they will be destroyed by the acid content in the stomach.

Further it is described in Eur. J. Clin. Microbiol. Infect. Dis, August 1988, p. 566–569 that some acid degradable antibiotics are active in vitro against *Helicobacter pylori*.

OUTLINE OF THE INVENTION

It has now unexpectedly been found that a combination of a substance with inhibiting effect on the gastric acid secretion, thus a substance which increases the intragastric pH e.g. proton pump inhibitors, histamin-$H_2$-blockers and one or more antibacterial compounds which is acid degradable give high plasma concentration of the antibiotic following oral administration.

By reducing the acidity in the stomach it is possible to markedly increase the bioavailability of acid-degradable antibiotics thus leaving more of a given dose of the compound available for local antibacterial effect as well as for absorption. Selection of narrow-spectrum antibiotics e.g. benzylpenicillin is favourable since such antibiotics have few side-effects. Due to known physico-chemical properties in general of weak bases like for instance omeprazole, the selection of weak bases e.g. erythromycin favours an increased accumulation of the antibiotic in the stomach wall and gastric crypts where the microbs e.g. *Helicobacter pylori* resides.

Thus, by combining the components of the present invention synergism of the antibacterial effect of antibiotic compounds is achieved resulting in an improved therapeutic efficacy.

DETAILED DESCRIPTION OF THE INVENTION

Figure 1:
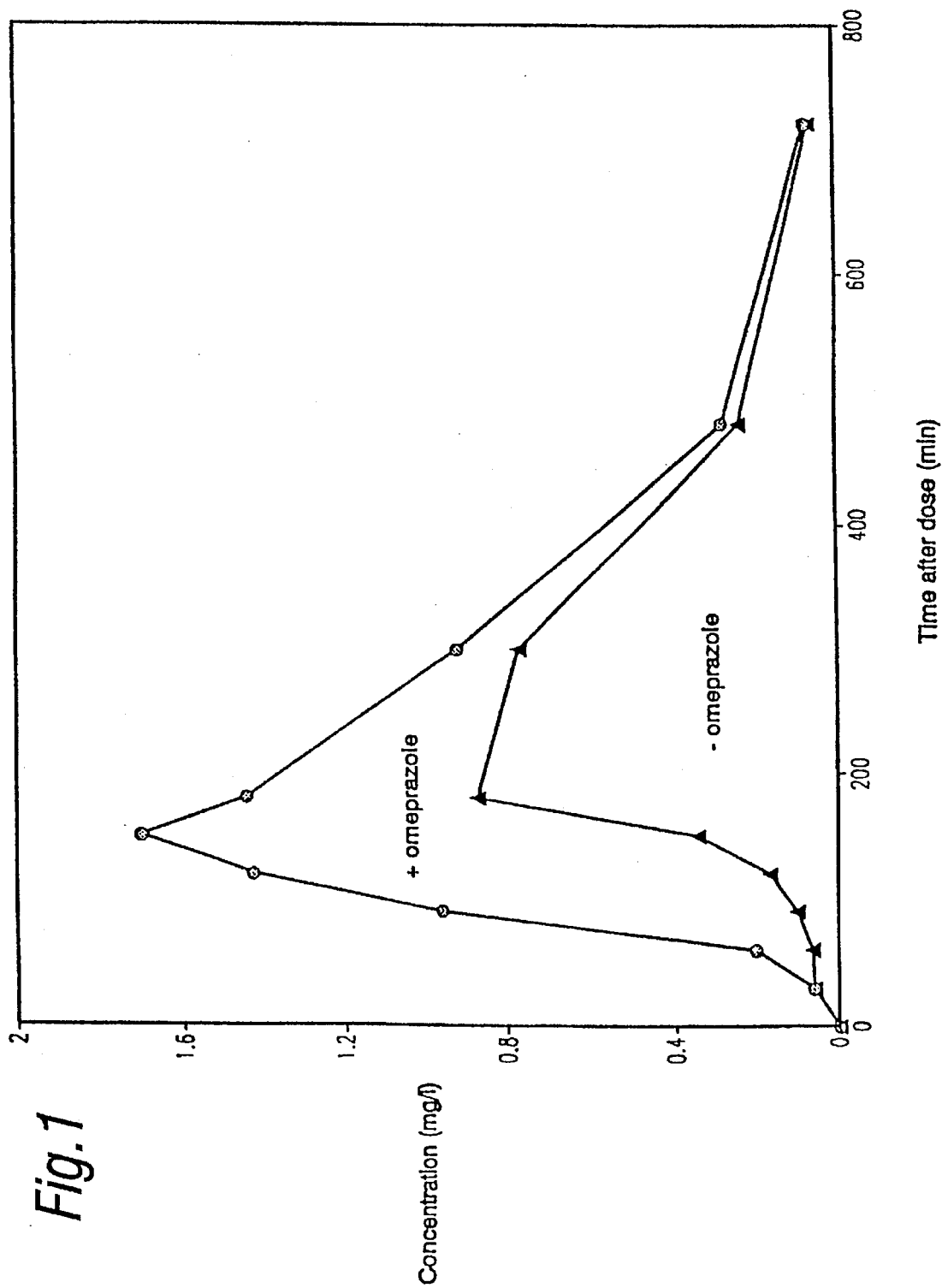
FIG. 1 represents a graph showing the blood serum levels of erythromycin Ery-Max® in healthy subjects during treatment with and without omeprazole.

The new combination is especially directed to the treatment of gastropathies e.g. induced by *Helicobacter pylori* infections. *Helicobacter pylori* is a gram-negative spirilliform bacterium which colonises in the gastric mucosa. Treatment with commonly used acid degradable antibiotics alone has given insufficient effect.

The combination of 5-methoxy-2-([(4-methoxy-3,5-dimethyl- 2-pyridinyl)methyl]sulfinyl)-1H-benzimidazole (generic name: omeprazole) or pharmaceutically acceptable salts thereof and an acid degradable antibiotic give an especially high plasma concentration of the antibiotic following oral administration.

The salt of omeprazole according to the invention is an alkaline pharmaceutically acceptable salt. Examples of such salts include inorganic salts, such as alkali metal salts, e.g. sodium salt, potassium salt etc., alkaline earth metal salts, e.g. calcium salt, magnesium salt etc., ammonium salt, organic salts such as organic amine salts, e.g. trimethylamine salt, triethylamine salt, pyridine salt, procaine acid, picoline salt, dicyclohexylamine salt, N,N-dibenzylethylenediamine salt, N-methylglucamine salt, diethanolamine salt, triethanolamine salt, tris (hydroxymethylamino)methane salt, phenylethylbenzylamine salt, dibenzylethylenediamine salt.

Also other proton pump inhibitors, such as lansoprazole may be used according to the invention. The antibiotic used in the combination should be of the kind, which has a bioavailability which may be improved due to elevation of intragastric pH. It should also be an antimicrobial compound with a very narrow spectrum e.g. benzylpenicillin.

Other examples are acid degradable and acid semi-stable macrolides e.g. erythromycin base and clarithromycin (Nakagawa et al., Chem. Pharm. Bull., 1992, 40, 725–28). Further examples are antibiotics and/or salts thereof which are pharmaceutically enginered for acid protection like for instance enteric coating (e.g. Ery-Max®).

The antibacterial activity against *Helicobacter pylori* as indicated by MIC-values of macrolides is drastically decreased with increased pH of the medium in vitro (Melanoski et al., ICAAC, 1992, abstract 713, p 229).

The combination according to the present invention can be produced in one pharmaceutical formulation comprising both active ingredients or in two separate tablets or capsules, powder, mixture, effervescence tablets or solution.

The active ingredients according to the invention are administered in the form of a pharmaceutical preparation containing the active ingredients as such (e.g. the free base in the case of erythromycin) or in the case of omeprazole also as a salt thereof in combination with a pharmaceutically acceptable carrier by the oral or parenteral route. The carrier mentioned above may be a solid, semi-solid or liquid diluent or a capsule. Compatible dosage forms include various types of tablets, capsules, granules, powders, oral liquids, injections and so on. The proportions of the active ingredient in the total composition is generally 0.1 to 100 weight percent and preferably 0.1 to 95 weight precent.

In the manufacture of a pharmaceutical preparation for oral administration, the active ingredient can be formulated with a solid particulate carrier such as lactose, sucrose, sorbitol, mannitol, starch, amylopectin, a cellulose derivative or gelatin, and a lubricating agent such as magnesium stearate, calcium stearate or polyethylene glycol wax may be further incorporated. The resulting composition is then compressed into tablets. Coated tablets or dragees can be manufactured by coating the core tablets, thus prepared, with a thick sugar solution containing gum arabic, gelatin, talc, titanium dioxide, etc. or a lacquer prepared using a volatile organic solvent or solvent mixture.

Soft gelatin capsules can be manufactured by filling a composition comprising the active ingredient and a known vegetable oil into capsules. Hard gelatin capsules can be manufactured by filling into capsules the granules or pellets each comprising the active ingredient and a solid particulate carrier such as lactose, sucrose, sorbitol, mannitol, potato starch, corn starch, amylopectin, a cellulose derivative or gelatin.

The dosage of omeprazole or a salt thereof and the antibiotic depends on individual needs (for example, the patient's condition, body weight, age, sex, etc.) as well as on the method of administration. Generally speaking, the oral dosage may range from 1 to 200 mg of omeprazole per day and up to 10 g of acid degradable antibiotic per adult human. Each may be administered in one to a few divided doses.

PHARMACOLOGICAL TESTS

Figure 2:
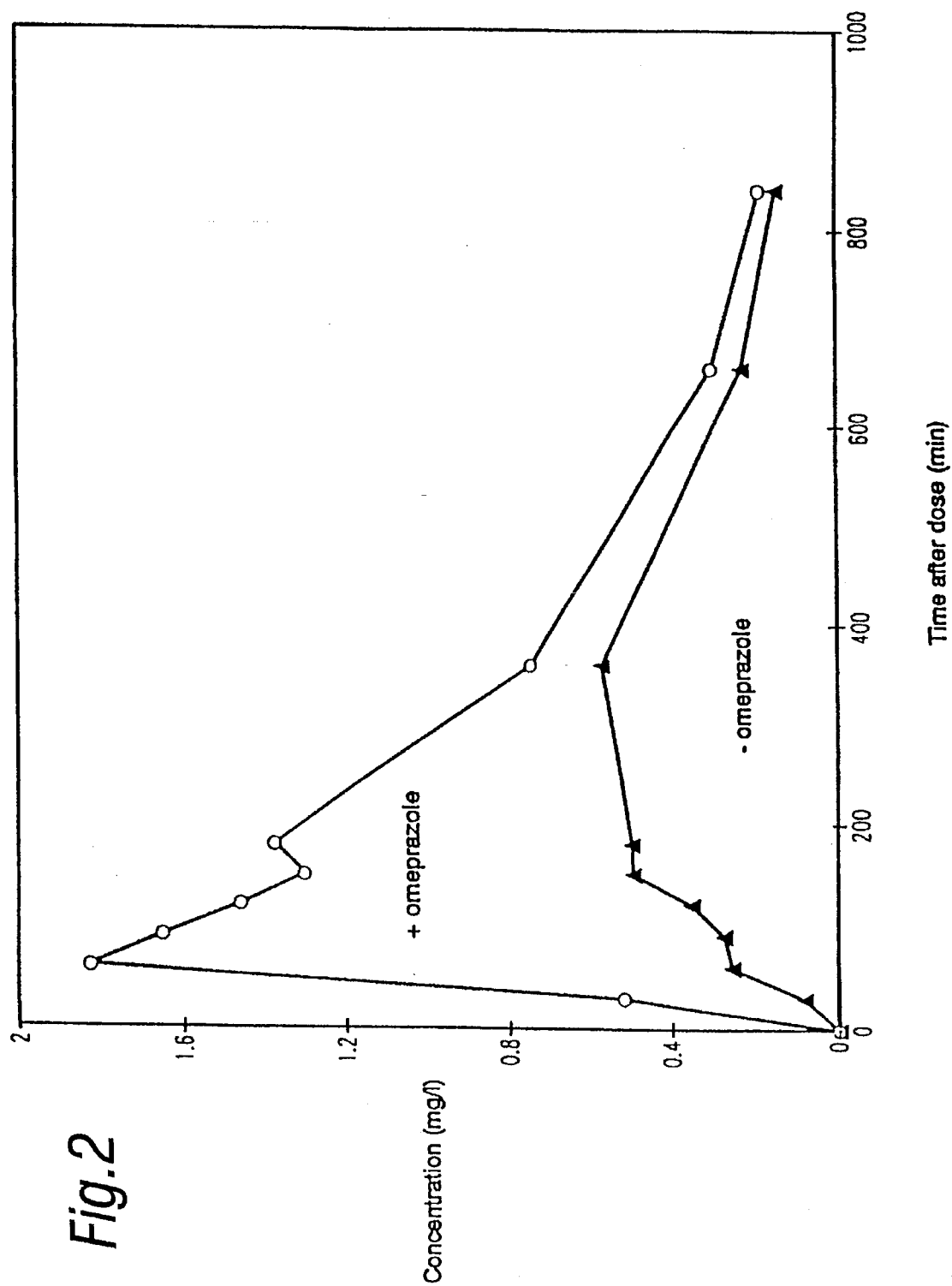
FIG. 2 represents a graph showing the blood serum levels of clarithromycin in healthy subjects during treatment with and without omeprazole.

Benzylpenicillin was administered alone to eight healthy volunteers and in combination with omeprazole and the plasma concentration was measured. When benzylpenicillin was administered alone the plasma concentrations, which were expressed in terms of the area under the plasma concentration-time curve, AUC (mg-h/L), and the maximum concentration, $C_{max}$ (mg/L), and time, T, or maximum time, $T_{max}$ (h or min), were insufficient for a therapeutical effect (Table 1). When benzylpenicillin was combined with omeprazole therapeutical useful plasma concentrations were reached (Table 2). Similar results were obtained after oral administration of erythromycin lactobionate prior and after omeprazole induced reduction of acid secretion in man (Tables 3 and 4). Semidegradable macrolides, e.g. Ery-Max® and clarithromycin are absorbed to a certain extent (Tables 5 and 7). However, after administration of an acid secretion inhibitor, omeprazole, a marked increase of the bioavailability of the macrolides is shown as indicated by the difference in $C_{max}$ and AUC in healthy volunteers (Tables 6 and 8). Compare also FIG. 1 and FIG. 2 showing the accurate plasma concentrations of Ery-Max® and clarithromycin with and without omeprazole. The high plasma concentrations of the antibiotics after reduction of the gastric acid secretion is evidence for a great reduction of the degradation in the stomach of the antibiotics used. This results in an increased amount of the active antibiotic in the gastric lumen, thus resulting in increased local antimicrobial effect. It also leads to a larger amount of the antibiotic available for absorption, thus resulting in increased plasma and tissue levels of the antibiotic (increased bioavailability). The best mode of carrying out the invention at present is to combine omeprazole with erythromycin.

TABLE 1

Concentration in plasma of benzylpenicillin after oral administration Dose 1.0 g. (without omeprazole)

| Person number | Plasma concentration mg/L | | | | | | | | | Cmax mg/L | AUC H · mg/L |
|---|---|---|---|---|---|---|---|---|---|---|---|
| | 15' | 30' | 45' | 1 h | 1.5 h | 2 h | 3 h | 4 h | 6 h | | |
| 1 | 0.24 | 0.50 | 0.54 | 0.41 | 0.22 | 0.135 | 0.074 | <0.02 | <0.02 | 0.54 | 0.81 |
| 2 | 0.53 | 1.60 | 1.47 | 1.24 | 0.52 | 0.30 | 0.14 | 0.063 | <0.02 | 1.60 | 2.06 |
| 3 | 0.23 | 0.51 | 0.45 | 0.37 | 0.21 | 0.11 | 0.051 | 0.016 | <0.02 | 0.51 | 0.69 |
| 4 | 0.076 | 0.23 | 0.20 | 0.15 | 0.084 | 0.053 | 0.044 | 0.023 | <0.02 | 0.23 | 0.38 |
| 5 | 0.26 | 0.50 | 0.41 | 0.40 | 0.28 | 0.17 | 0.071 | 0.042 | <0.02 | 0.50 | 0.84 |
| 6 | 0.33 | 0.37 | 0.26 | 0.20 | 0.099 | 0.051 | 0.038 | <0.02 | <0.02 | 0.37 | 0.48 |
| 7 | 0.17 | 0.26 | 0.23 | 0.17 | 0.14 | 0.075 | 0.027 | <0.02 | <0.02 | 0.26 | 0.39 |
| 8 | 0.104 | 0.125 | 0.124 | 0.121 | 0.062 | 0.050 | 0.021 | <0.02 | <0.02 | 0.125 | 0.24 |
| Mean value | 0.24 | 0.51 | 0.46 | 0.38 | 0.20 | 0.118 | 0.058 | <0.03 | <0.02 | 0.52 | 0.74 |
| ± S.D. | | | | | | | | | | 0.46 | 0.58 |

Cmax:tdep = 4.163 P < 0.01
AUC:tdep = 5.553 P < 0.001

TABLE 2

Concentration in plasma of benzylpenicillin after oral administration Dose 1.0 g.
(with omeprazole)

| Person number | Plasma concentration mg/L | | | | | | | | | Cmax mg/L | AUC H · mg/L |
|---|---|---|---|---|---|---|---|---|---|---|---|
| | 15' | 30' | 45' | 1 h | 1.5 h | 2 h | 3 h | 4 h | 6 h | | |
| 1 | 0.89 | 2.98 | 3.25 | 3.41 | 3.74 | 2.79 | 0.89 | 0.70 | 0.25 | 3.74 | 9.54 |
| 2 | 0.73 | 2.80 | 5.51 | 5.74 | 2.26 | 1.62 | 0.84 | 0.76 | 0.28 | 5.74 | 9.52 |
| 3 | 1.40 | 6.24 | 9.85 | 9.75 | 6.59 | 1.67 | 0.53 | 0.30 | 0.061 | 9.85 | 13.20 |
| 4 | 0.11 | 0.72 | 1.22 | 3.05 | 7.57 | 5.59 | 2.94 | 0.45 | 0.094 | 7.57 | 12.80 |
| 5 | 0.64 | 2.48 | 2.45 | 2.10 | 1.95 | 1.10 | 0.46 | 0.25 | 0.054 | 2.48 | 4.82 |
| 6 | 1.24 | 3.22 | 3.65 | 3.57 | 1.42 | 0.84 | 0.55 | 0.33 | 0.074 | 3.65 | 5.78 |
| 7 | 0.33 | 0.83 | 1.43 | 1.52 | 1.17 | 0.87 | 0.45 | 0.21 | 0.074 | 1.52 | 3.34 |
| 8 | 0.62 | 1.37 | 2.31 | 2.35 | 2.54 | 1.37 | 0.48 | 0.23 | 0.041 | 2.54 | 5.00 |
| Mean value | 0.745 | 2.58 | 3.71 | 3.94 | 3.41 | 1.98 | 0.89 | 0.40 | 0.116 | 4.64 | 8.00 |
| ± S.D. | | | | | | | | | | 2.87 | 3.79 |

Cmax:tdep = 4.163 P < 0.01
AUC:tdep = 5.553 P < 0.001

TABLE 3

Concentration in plasma of erythromycin lactobionate after oral a inistration. Dose 1.0 g.
1(2) Without preceding omeprazole treatment

| Subjects number | Serum levels in mg/L at indicated times | | | | | | | | | |
|---|---|---|---|---|---|---|---|---|---|---|
| | 0 | 15' | 30' | 45' | 1 h | 1.5 h | 2 h | 3 h | 4 h | 6 h |
| 1 | <0.015 | 0.015 | 0.15 | 0.29 | 0.28 | 0.20 | 0.18 | 0.13 | 0.091 | 0.047 |
| 2 | <0.015 | 0.26 | 0.33 | 0.30 | 0.25 | 0.25 | 0.18 | 0.15 | 0.16 | 0.070 |
| 3 | <0.015 | 0.042 | 0.22 | 0.21 | 0.24 | 0.14 | 0.13 | 0.12 | 0.86 | 0.049 |
| 4 | <0.015 | 0.032 | 0.042 | 0.030 | 0.039 | 0.078 | 0.084 | 0.076 | 0.072 | 0.046 |
| 5 | <0.015 | 0.023 | 0.13 | 0.16 | 0.16 | 0.15 | 0.14 | 0.12 | 0.082 | 0.051 |
| 6 | <0.015 | 0.068 | 0.12 | 0.094 | 0.11 | 0.098 | 0.077 | 0.074 | 0.059 | 0.034 |
| 7 | <0.015 | 0.57 | 0.98 | 0.75 | 0.68 | 0.43 | 0.37 | 0.32 | 0.27 | 0.088 |
| 8 | <0.015 | 0.071 | 0.27 | 0.33 | 0.23 | 0.16 | 0.16 | 0.12 | 0.095 | 0.044 |
| Mean value | <0.015 | 0.135 | 0.28 | 0.27 | 0.25 | 0.18 | 0.165 | 0.14 | 0.11 | 0.054 |
| ± S.D. | | ±0.193 | ±0.30 | ±0.22 | ±0.19 | ±0.11 | ±0.092 | ±0.078 | ±0.070 | ±0.017 |

TABLE 3

Concentration in plasma of erythromycin lactobionate after oral administration. Dose 1.0 g.
2(2) With preceding omeprazole treatment

| Subject number | Serum levels in mg/L at indicated times | | | | | | | | | |
|---|---|---|---|---|---|---|---|---|---|---|
| | 0 | 15' | 30' | 45' | 1 h | 1.5 h | 2 h | 3 h | 4 h | 6 h |
| 1 | <0.015 | 2.9 | 7.5 | 7.6 | 7.2 | 4.9 | 4.0 | 3.1 | 3.5 | 1.4 |
| 2 | <0.015 | 2.3 | 6.8 | 5.7 | 4.5 | 5.3 | 3.6 | 3.3 | 3.2 | 1.4 |
| 3 | <0.015 | 2.7 | 12.7 | 10.9 | 7.8 | 6.0 | 5.3 | 4.5 | 4.0 | 2.4 |
| 4 | <0.015 | 3.2 | 6.0 | 3.3 | 2.5 | 1.9 | 2.8 | 2.4 | 2.4 | 0.82 |
| 5 | <0.015 | 0.25 | 2.8 | 6.4 | 4.8 | 3.0 | 2.5 | 2.0 | 2.8 | 1.2 |
| 6 | <0.015 | 1.5 | 4.9 | 3.4 | 2.7 | 1.6 | 1.8 | 1.6 | 2.1 | 0.89 |
| 7 | <0.015 | 6.3 | 9.8 | 9.3 | 6.2 | 5.3 | 4.6 | 4.6 | 3.9 | 1.8 |
| 8 | <0.015 | 3.8 | 12.8 | 13.0 | 11.1 | 10.7 | 7.3 | 5.6 | 4.3 | 2.2 |
| Mean value | <0.015 | 2.87 | 7.91 | 7.45 | 5.85 | 4.84 | 3.99 | 3.39 | 3.28 | 1.51 |
| ± S.D. | | ±1.77 | ±3.60 | ±3.46 | ±2.86 | ±1–2.89 | ±1.76 | ±1.40 | ±0.79 | ±0.58 |

TABLE 4

Kinetic data following oral administration(s) of erythromycin lactobionate to 8 healthy volunteers with and without co-administration of omeprazole. A cross over study.

| Omeprazole | $C_{max}$ mg/L mean ± SD | $T_{max}$ h median | AUC H · mg/L 0–6 H |
|---|---|---|---|
| YES | 8.38 ±0.28 | 0.5 | 21.74 ± 8.64 |
| NO | 0.32 ±0.28 | 0.75 | 0.83 ± 0.55 |

TABLE 5

Blood serum levels of erythromycin Ery-Max ® following oral administration. Dose 500 mg.
1(2) Without preceding omeprazole treatment.

| Subject number | Serum levels in mg/L at indicated times (min) | | | | | | | | | |
|---|---|---|---|---|---|---|---|---|---|---|
| | 0 | 30 | 60 | 90 | 120 | 150 | 180 | 300 | 480 | 720 |
| 1 | 0.00 | 0.06 | 0.06 | 0.06 | 0.12 | 0.28 | 1.90 | 0.76 | 0.15 | 0.06 |
| 2 | 0.00 | 0.06 | 0.06 | 0.06 | 0.06 | 0.06 | 0.06 | 0.65 | 0.19 | 0.06 |
| 3 | 0.00 | 0.06 | 0.06 | 0.06 | 0.06 | 0.08 | 0.75 | 0.49 | 0.20 | 0.06 |
| 4 | 0.00 | 0.06 | 0.06 | 0.06 | 0.06 | 0.16 | 0.43 | 0.92 | 0.25 | 0.07 |
| 5 | 0.00 | 0.06 | 0.06 | 0.06 | 0.06 | 0.25 | 0.95 | 1.50 | 0.45 | 0.07 |
| 6 | 0.00 | 0.06 | 0.06 | 0.06 | 0.06 | 0.06 | 0.06 | 0.52 | 0.17 | 0.06 |
| 7 | 0.00 | 0.06 | 0.10 | 0.38 | 0.41 | 0.68 | 1.10 | 0.46 | 0.20 | 0.06 |
| 8 | 0.00 | 0.06 | 0.06 | 0.06 | 0.51 | 1.20 | 1.70 | 0.86 | 0.31 | 0.06 |
| Mean | 0.00 | 0.06 | 0.07 | 0.10 | 0.17 | 0.35 | 0.87 | 0.77 | 0.24 | 0.06 |
| Sdev | 0.00 | 0.00 | 0.01 | 0.11 | 0.18 | 0.40 | 0.69 | 0.34 | 0.10 | 0.01 |

TABLE 5

Blood serum levels of erythromycin Ery-Max ® following oral administration. Dose 500 mg.
2(2) Without preceding omeprazole treatment.

| Subject number | AUC levels at indicated times (min) | | | | | | | | | | Tot AUC |
|---|---|---|---|---|---|---|---|---|---|---|---|
| | 0 | 30 m | 60 m | 90 m | 120 m | 150 m | 180 m | 300 m | 480 m | 720 m | |
| 1 | 0 | 0.015 | 0.03 | 0.03 | 0.045 | 0.1 | 0.545 | 2.66 | 1.365 | 0.42 | 5.21 |
| 2 | 0 | 0.015 | 0.03 | 0.03 | 0.03 | 0.03 | 0.03 | 0.71 | 1.26 | 0.5 | 2.635 |
| 3 | 0 | 0.015 | 0.03 | 0.03 | 0.03 | 0.036 | 0.208 | 1.24 | 1.035 | 0.52 | 3.144 |
| 4 | 0 | 0.015 | 0.03 | 0.03 | 0.03 | 0.055 | 0.148 | 1.35 | 1.755 | 0.646 | 4.059 |
| 5 | 0 | 0.015 | 0.03 | 0.03 | 0.03 | 0.078 | 0.3 | 2.45 | 2.925 | 1.036 | 6.894 |
| 6 | 0 | 0.015 | 0.03 | 0.03 | 0.03 | 0.03 | 0.03 | 0.58 | 1.035 | 0.46 | 2.24 |
| 7 | 0 | 0.015 | 0.04 | 0.12 | 0.198 | 0.273 | 0.445 | 1.56 | 0.99 | 0.52 | 4.16 |
| 8 | 0 | 0.015 | 0.03 | 0.03 | 0.143 | 0.428 | 0.725 | 2.56 | 1.755 | 0.74 | 6.425 |
| Mean | 0 | 0.015 | 0.031 | 0.041 | 0.067 | 0.129 | 0.304 | 1.639 | 1.515 | 0.605 | |
| Sdev | 0 | 0.015 | 0.004 | 0.032 | 0.066 | 0.145 | 0.25 | 0.827 | 0.647 | 0.202 | |

AUC: 4.34 ± 1.7
$C_{max}$: 1.005

TABLE 6

Blood serum levels of erythromycin Ery-Max ® following oral administration.
Dose 250 mg.
1(2) With preceding omeprazole treatment.

| Subject number | Serum levels in mg/L at indicated times (min) | | | | | | | | | |
|---|---|---|---|---|---|---|---|---|---|---|
| | 0 | 30 m | 60 m | 90 m | 120 m | 150 m | 180 m | 300 m | 480 m | 720 m |
| 1 | 0.00 | 0.06 | 0.54 | 3.2 | 2.4 | 2.3 | 1.9 | 0.79 | 0.22 | 0.06 |
| 2 | 0.00 | 0.06 | 0.06 | 0.1 | 0.69 | 2.1 | 1.7 | 0.54 | 0.14 | 0.06 |
| 3 | 0.00 | 0.06 | 0.29 | 1.2 | 2.5 | 2.5 | 1.4 | 0.75 | 0.23 | 0.06 |
| 4 | 0.00 | 0.06 | 0.06 | 0.094 | 0.84 | 0.74 | 0.37 | 1.3 | 0.45 | 0.081 |
| 5 | 0.00 | 0.06 | 0.06 | 0.059 | 0.58 | 1.5 | 1.7 | 1.6 | 0.5 | 0.084 |
| 6 | 0.00 | 0.06 | 0.068 | 0.49 | 1.2 | 0.86 | 0.68 | 0.48 | 0.14 | 0.06 |
| 7 | 0.00 | 0.06 | 0.057 | 1.1 | 1.3 | 2 | 2.1 | 0.87 | 0.27 | 0.087 |
| 8 | 0.00 | 0.06 | 0.48 | 1.4 | 1.9 | 1.6 | 1.7 | 1 | 0.28 | 0.084 |
| Mean | 0.00 | 0.06 | 0.20 | 0.96 | 1.43 | 1.7 | 1.44 | 0.92 | 0.28 | 0.07 |
| Sdev | 0.00 | 0.00 | 0.21 | 1.06 | 0.76 | 0.65 | 0.61 | 0.38 | 0.13 | 0.01 |

TABLE 6

Blood serum levels of erythromycin Ery-Max ® following oral administration. Dose 250 mg.
2(2) With preceding omeprazole treatment.

| Subject number | AUC levels at indicated times (min) | | | | | | | | | | |
|---|---|---|---|---|---|---|---|---|---|---|---|
| | 0 | 30 m | 60 m | 90 m | 120 m | 150 m | 180 m | 300 m | 480 m | 720 m | Tot AUC |
| 1 | 0.00 | 0.015 | 0.15 | 0.935 | 1.4 | 1.175 | 1.05 | 2.69 | 1.515 | 0.56 | 9.49 |
| 2 | 0.00 | 0.015 | 0.03 | 0.04 | 0.198 | 0.698 | 0.95 | 2.24 | 1.02 | 0.4 | 5.59 |
| 3 | 0.00 | 0.015 | 0.088 | 0.373 | 0.925 | 1.25 | 0.975 | 2.15 | 1.47 | 0.58 | 7.825 |
| 4 | 0.00 | 0.015 | 0.03 | 0.039 | 0.234 | 0.395 | 0.278 | 1.67 | 2.625 | 1.062 | 6.347 |
| 5 | 0.00 | 0.015 | 0.03 | 0.03 | 0.16 | 0.52 | 0.8 | 3.3 | 3.15 | 1.168 | 9.173 |
| 6 | 0.00 | 0.015 | 0.032 | 0.14 | 0.423 | 0.515 | 0.385 | 1.16 | 0.93 | 0.4 | 3.999 |
| 7 | 0.00 | 0.015 | 0.029 | 0.289 | 0.6 | 0.825 | 1.025 | 2.97 | 1.71 | 0.714 | 8.187 |
| 8 | 0.00 | 0.015 | 0.0135 | 0.47 | 0.825 | 0.875 | 0.825 | 2.7 | 1.92 | 0.728 | 8.493 |
| Mean | 0.00 | 0.015 | 0.065 | 0.289 | 0.595 | 0.782 | 0.786 | 2.36 | 1.793 | 0.702 | |
| Sdev | 0.00 | 0.00 | 0.052 | 0.31 | 0.434 | 0.312 | 0.295 | 0.703 | 0.764 | 0.284 | |

AUC: 7.38 ± 1.9
$C_{max}$: 1.94

TABLE 7

Blood serum levels of clarithromycin following oral administration. Dose 250 mg.
1(2) Without preceding omeprazole treatment.

| Subject number | Serum levels in mg/L at indicated times (min) | | | | | | | | | |
|---|---|---|---|---|---|---|---|---|---|---|
| | 0 | 30 m | 60 m | 90 m | 120 m | 150 m | 180 m | 360 m | 660 m | 840 m |
| 1 | 0.00 | 0.11 | 0.97 | 0.92 | 1.1 | 1.5 | 1.2 | 0.96 | 0.41 | 0.26 |
| 2 | 0.00 | 0.12 | 0.15 | 0.24 | 0.28 | 0.36 | 0.47 | 0.53 | 0.18 | 0.14 |
| 3 | 0.00 | 0.06 | 0.11 | 0.092 | 0.11 | 0.12 | 0.17 | 0.55 | 0.2 | 0.12 |
| 4 | 0.00 | 0.06 | 0.06 | 0.044 | 0.099 | 0.13 | 0.15 | 0.48 | 0.23 | 0.13 |
| 5 | 0.00 | 0,06 | 0.06 | 0.062 | 0.064 | 0.13 | 0.18 | 0.54 | 0.2 | 0.16 |
| 6 | 0.00 | 0.07 | 0.13 | 0.2 | 0.3 | 0.37 | 0.45 | 0.23 | 0.14 | 0.082 |
| 7 | 0.00 | 0.12 | 0.26 | 0.27 | 0.46 | 0.81 | 0.78 | 0.64 | 0.2 | 0.12 |
| 8 | 0.00 | 0.06 | 0.31 | 0.38 | 0.41 | 0.55 | 0.57 | 0.64 | 0.27 | 0.16 |
| Mean | 0.00 | 0.08 | 0.26 | 0.28 | 0.35 | 0.50 | 0.50 | 0.57 | 0.23 | 0.15 |
| Sdev | 0.00 | 0.03 | 0.30 | 0.28 | 0.34 | 0.47 | 0.36 | 0.20 | 0.08 | 0.05 |

TABLE 7

Blood serum levels of clarithromycin following oral administration. Dose 250 mg.
2(2) Without preceding omeprazole treatment.

| Subject number | AUC levels at indicated times (min) | | | | | | | | | | Tot AUC |
|---|---|---|---|---|---|---|---|---|---|---|---|
| | 0 | 30 m | 60 m | 90 m | 120 m | 150 m | 180 m | 360 m | 660 m | 840 m | |
| 1 | 0.00 | 0.028 | 0.27 | 0.473 | 0.505 | 0.65 | 0.675 | 2.16 | 4.11 | 1.005 | 9.895 |
| 2 | 0.00 | 0.03 | 0.068 | 0.098 | 0.13 | 0.16 | 0.208 | 1 | 2.13 | 0.48 | 4.303 |
| 3 | 0.00 | 0.015 | 0.043 | 0.051 | 0.051 | 0.058 | 0.073 | 0.72 | 2.25 | 0.48 | 3.739 |
| 4 | 0.00 | 0.015 | 0.03 | 0.026 | 0.036 | 0.057 | 0.07 | 0.63 | 2.13 | 0.54 | 3.534 |
| 5 | 0.00 | 0.015 | 0.03 | 0.031 | 0.032 | 0.049 | 0.078 | 0.72 | 2.22 | 0.54 | 3.713 |
| 6 | 0.00 | 0.018 | 0.05 | 0.083 | 0.125 | 0.168 | 0.205 | 0.68 | 1.11 | 0.333 | 2.771 |
| 7 | 0.00 | 0.03 | 0.095 | 0.133 | 0.183 | 0.318 | 0.398 | 1.42 | 2.52 | 0.48 | 5.575 |
| 8 | 0.00 | 0.015 | 0.093 | 0.173 | 0.198 | 0.24 | 0.28 | 1.21 | 2.73 | 0.645 | 5.583 |
| Mean | 0.00 | 0.021 | 0.085 | 0.133 | 0.157 | 0.212 | 0.248 | 1.068 | 2.4 | 0.563 | |
| Sdev | 0.00 | 0.007 | 0.079 | 0.146 | 0.154 | 0.201 | 0.207 | 0.525 | 0.838 | 0.199 | |

AUC: 4.88 ± 2.24
$C_{max}$: 0.68

TABLE 8

Blood serum levels of clarithromycin following oral administration. Dose 250 mg.
1(2) With preceding omeprazole treatment.

| Subject number | Serum levels in mg/L at indicated times (min) | | | | | | | | | |
|---|---|---|---|---|---|---|---|---|---|---|
| | 0 | 30 | 60 | 90 | 120 | 150 | 180 | 360 | 660 | 840 |
| 1 | 0.00 | 1.9 | 2.3 | 2.2 | 1.7 | 1.7 | 1.7 | 0.86 | 0.37 | 0.28 |
| 2 | 0.00 | 0.078 | 3 | 1.9 | 1.9 | 1.9 | 1.7 | 0.78 | 0.34 | 0.16 |
| 3 | 0.00 | 0.6 | 1.6 | 1.3 | 1.1 | 1.1 | 1.05 | 0.68 | 0.23 | 0.14 |
| 4 | 0.00 | 0.06 | 1.2 | 1.3 | 1.2 | 1.03 | 1.1 | 0.68 | 0.39 | 0.2 |
| 5 | 0.00 | 0.096 | 2.1 | 1.6 | 1.3 | 1.1 | 1.1 | 0.77 | 0.27 | 0.18 |
| 6 | 0.00 | 0.21 | 1.2 | 1.8 | 1.6 | 1 | 1.5 | 0.67 | 0.22 | 0.13 |
| 7 | 0.00 | 0.12 | 0.99 | 1.1 | 0.9 | 0.89 | 1.07 | 0.61 | 0.22 | 0.16 |
| 8 | 0.00 | 1.07 | 2.2 | 2 | 2 | 1.7 | 1.8 | 0.92 | 0.38 | 0.24 |
| Mean | 0.00 | 0.52 | 1.82 | 1.65 | 1.46 | 1.30 | 1.38 | 0.75 | 0.30 | 0.19 |
| Sdev | 0.00 | 0.66 | 0.69 | 0.39 | 0.40 | 0.39 | 0.33 | 0.11 | 0.08 | 0.05 |

TABLE 8

Blood serum levels of clarithromycin following oral administration. Dose 250 mg.
2(2) With preceding omeprazole treatment.

| Subject number | AUC levels at indicated times (min) | | | | | | | | | | Tot AUC |
|---|---|---|---|---|---|---|---|---|---|---|---|
| | 0 | 30 | 60 | 90 | 120 | 150 | 180 | 360 | 660 | 840 | |
| 1 | 0.00 | 0.475 | 1.05 | 1.125 | 0.975 | 0.85 | 0.85 | 2.56 | 3.69 | 0.975 | 12.55 |
| 2 | 0.00 | 0.02 | 0.77 | 1.225 | 0.95 | 0.95 | 0.9 | 2.48 | 3.36 | 0.75 | 11.4 |
| 3 | 0.00 | 0.15 | 0.55 | 0.725 | 0.6 | 0.55 | 0.538 | 1.73 | 2.73 | 0.555 | 8.128 |
| 4 | 0.00 | 0.015 | 0.315 | 0.625 | 0.625 | 0.558 | 0.533 | 1.78 | 3.21 | 0.885 | 8.545 |
| 5 | 0.00 | 0.024 | 0.549 | 0.925 | 0.725 | 0.6 | 0.55 | 1.87 | 3.12 | 0.675 | 9.038 |
| 6 | 0.00 | 0.053 | 0.353 | 0.75 | 0.85 | 0.65 | 0.625 | 2.17 | 2.67 | 0.525 | 8.645 |
| 7 | 0.00 | 0.03 | 0.278 | 0.523 | 0.5 | 0.448 | 0.49 | 1.68 | 2.49 | 0.57 | 7.008 |
| 8 | 0.00 | 0.268 | 0.818 | 1.05 | 1 | 0.925 | 0.875 | 2.72 | 3.9 | 0.93 | 12.49 |
| Mean | 0.00 | 0.129 | 0.585 | 0.868 | 0.778 | 0.691 | 0.67 | 2.124 | 3.146 | 0.733 | |
| Sdev | 0.00 | 0.165 | 0.275 | 0.251 | 0.192 | 0.191 | 0.174 | 0.416 | 0.499 | 0.18 | |

AUC: 9.7 ± 2.1
$C_{max}$: 1.9

DISCUSSION

The advantage of the present combination of a compound that increases the intragastric pH, such as omeprazole and an acid degradable antibiotic, is that the bioavailability of the antibiotic will increase resulting in sufficient plasma levels for therapeutic effects. Another advantage is that there will be increased amounts of the acid degradable antibiotic in the gastric lumen.

Benzylpenicillin is interesting because it has a very narrow spectrum and therefore exerts a very limited effect on the normal intestinal flora.

By reducing the gastric acid secretion or acid neutralisation in the stomach the pH increases. Due to the less acidic milieu the orally administered acid degradable antibiotic will be less catabolized and thus locally exerting its antimicrobial effect, Another advantage is that increased amounts of the antibiotic will pass into the small intestine where it will be absorbed in biologically active form. Increasing the intragastric pH is also favourable for antibiotic efficacy as shown in vitro. If the pH of the medium where *Helicobacter pylori* is grown in vitro is reduced varying degrees below pH 7 the antibacterial properties rapidly decrease.

Those antibiotics which are weak bases e.g. macrolides will be excreted via the stomach wall due to its physico-chemical properties in congruence with other known weak bases i.e. nicotine, aminopurine and omeprazole (Larsson et al., Scand. J. Gastroenterol., 1983, 85, 900–7). Thus, the antibiotic weak base will be biologically concentrated in the stomach wall, where the bacteria (e.g. *Helicobacter pylori*) reside.

We claim:

1. A pharmaceutical composition for the treatment of gastritis and peptic ulcer comprising a therapeutically effective amount of a proton pump inhibitor which increases intragastric pH; and a therapeutically effective amount of an acid degradable antibacterial compound.

2. The composition according to claim 1 wherein the proton pump inhibitor is omeprazole, lansoprazole or a salt thereof.

3. The composition according to claim 1 wherein the acid degradable antibacterial compound is a weak base antibacterial compound.

4. The composition according to claim 1 wherein the acid degradable antibacterial compound is selected from the group consisting of a penicillin and a macrolide.

5. The composition according to claim 4 wherein the penicillin is benzylpenicillin and the macrolide is an erythromycin or a clarithromycin.

6. The composition according to claim 1 wherein the acid degradable antibacterial compound is clarithromycin.

7. An oral pharmaceutical composition for the treatment of gastritis and peptic ulcer caused by *Helicobacter pylori* infections comprising as active ingredients (a) a therapeutically effective amount of a proton pump inhibiting compound which thereby increases the intragastric pH; and (b) a therapeutically effective amount of at least one acid degradable antibacterial compound.

8. A synergistic pharmaceutical combination of a therapeutic amount ranging from about 1–200 mg of proton pump inhibiting compound or salt thereof, which increases intragastric pH; and a therapeutic amount ranging from about 250 mg to 10g of an acid degradable antibacterial compound for the treatment of gastritis and peptic ulcer.

9. The synergistic pharmaceutical combination according to claim 8 wherein the acid degradable antibiotic is selected from the group consisting of a penicillin and a macrolide.

10. A synergistic pharmaceutical combination comprising a therapeutic amount of omeprazole or salt thereof and a therapeutic amount of a erythromycin for the treatment of gastritis and peptic ulcer.

11. A synergistic pharmaceutical combination comprising a therapeutic amount of omeprazole or salt thereof and a therapeutic amount of an acid degradable penicillin for the treatment of gastritis and peptic ulcer.

12. A synergistic pharmaceutical combination comprising therapeutic amount of omeprazole or salt thereof and a therapeutic amount of benzylpenicillin for the treatment of gastritis and peptic ulcer.

13. A synergistic pharmaceutical combination comprising a therapeutic amount of lansoprazole or salt thereof and a therapeutic amount of an erythromycin for the treatment of gastritis and peptic ulcer.

14. A synergistic pharmaceutical combination comprising a therapeutic amount of lansoprazole or salt thereof and a therapeutic amount of clarithromycin for the treatment of gastritis and peptic ulcer.

15. A synergistic pharmaceutical combination comprising a therapeutic amount of lansoprazole or salt thereof and a therapeutic amount of a penicillin for the treatment of gastritis and peptic ulcer.

16. A method for treatment of gastritis and peptic ulcer caused by *Helicobacter pylori* comprising first orally administering to a patient suffering therefrom a therapeutically effective amount of a composition comprising a proton pump inhibiting compound which is an inhibitor of gastric acid secretion; and thereafter or concomitantly administering a therapeutically effective amount of an acid degradable antibacterial compound.

17. The method according to claim 16, wherein the acid degradable antibacterial compound is selected from the group consisting of a macrolide and a penicillin.

18. The method according to claim 17, wherein the macrolide is selected from the group consisting of an erythromycin and a clarithromycin.

19. The method according to claim 17, wherein the antibacterial compound is benzylpenicillin.

* * * * *